United States Patent [19]

Reich

[11] Patent Number: 5,006,997
[45] Date of Patent: Apr. 9, 1991

[54] PUMP DIAGNOSTIC SYSTEM

[75] Inventor: Sanford Reich, Providence, R.I.

[73] Assignee: Shiley Infusaid, Inc., Norwood, Mass.

[21] Appl. No.: 484,284

[22] Filed: Feb. 26, 1990

Related U.S. Application Data

[63] Continuation of Ser. No. 133,409, Dec. 15, 1987, abandoned.

[51] Int. Cl.$^5$ .............................................. A61M 5/00
[52] U.S. Cl. ..................................... 364/510; 364/558;
364/413.03; 364/413.07; 364/413.02; 340/611;
340/606; 604/27; 604/30; 604/31; 604/65;
128/DIG. 12; 128/748
[58] Field of Search ............ 364/509, 510, 556, 413.02,
364/413.03, 413.07; 340/603, 606–611;
128/DIG. 12, DIG. 13, 748; 604/27, 28, 30, 31,
65, 67, 131, 901

[56] References Cited

U.S. PATENT DOCUMENTS

| | | | |
|---|---|---|---|
| 4,265,241 | 5/1981 | Portner et al. | 604/131 |
| 4,360,019 | 11/1982 | Portner et al. | 604/131 |
| 4,395,259 | 7/1983 | Prestele et al. | 604/67 |
| 4,447,224 | 5/1984 | DeCant, Jr. et al. | 604/67 |
| 4,486,190 | 12/1984 | Reinicke | 604/67 |
| 4,511,355 | 4/1985 | Franetzki et al. | 604/131 |
| 4,715,852 | 12/1987 | Reinicke et al. | 604/131 |
| 4,718,893 | 1/1988 | Dorman et al. | 604/67 |
| 4,731,051 | 3/1988 | Fischell | 604/67 |
| 4,743,228 | 5/1988 | Butterfield | 604/65 |
| 4,776,842 | 10/1988 | Franetzki et al. | 604/67 |

Primary Examiner—Parshotam S. Lall
Assistant Examiner—Brian M. Mattson
Attorney, Agent, or Firm—Sughrue, Mion, Zinn Macpeak & Seas

[57] ABSTRACT

A method and apparatus to evaluate the performance of an implanted medication delivery device such as pumps and ports is described. In the case of a pump, the system measures ambient pressure and obtains two pressure measurements from the implanted device. One of these measurements is device reservoir pressure and the other is based on a disturbance pulse injected into the system at a point downstream of the reservoir. Based on those measurements and input calibration data, an expected flow rate is determined. The expected flow rate together with device refill data is in turn used to determine a normalized flow rate for the in-vivo device. Determinations are then made as to the performance of the reservoir, its pump and the condition of the outlet catheter without explant of the device. In the case of a port, the system measures the catheter resistance based on decay time of a disturbance pulse.

22 Claims, 2 Drawing Sheets

PUMP DIAGNOSTIC SYSTEM

This is a continuation of application Ser. No. 07/133,409, filed Dec. 15, 1987, now abandoned.

BACKGROUND OF THE INVENTION

This invention relates to a system for the diagnosis of flow related problems which may exist in implantable medication delivery devices. Those implantable flow devices include continuous pumps, programmable pumps, and ports. Typical is the INFUSAID Series 100 and 400 devices and INFUSE-A-PORT ports. The evaluation of in-vivo pump performance requires obtaining and monitoring measured flow data and pump system environmental conditions at various intervals. One typical time of determining performance of the in-vivo system is during refill of the pump wherein measured flow rates to the expected in-vivo port performance requires obtaining and monitoring catheter flow resistance.

There are a variety of problems which may cause variations in such performance. For example, in-vivo pump temperature may differ from the assumed constant body core temperature. This will effect the pump flow by varying the 2-phase vapor pressure of the pressurizing material, typically Freon. Variation in in-vivo pump temperature may also vary the viscosity of the medication. Another parameter that effects pump flow is the presence of any resistance at the catheter tip.

In the case of sideport access systems such as the INFUSAID 400, it is possible to separate a diagnosis of pump operating parameters from those of the catheter. A determination of the separate flow problems for the pump and catheter are important since a malfunctioning pump would not require recatheterization and a malfunctioning catheter would not require a pump explant. Thus, in situations where the in-vivo device utilizes a sideport, either integral or separate, diagnosis of catheters attached to the pumps can be used to measure the pressure at the inlet to the catheter. In those systems, then, a requirement exists to differentiate pump flow problems from catheter flow problems.

In the past, fluoroscopic examination of the catheter in a blood vessel, while injecting a contrast agent, has been attempted as a technique to determine the presence of any resistant elements at the catheter tip. Such visual techniques, however, do not provide sufficient information to fully evaluate catheter performance.

SUMMARY OF THE INVENTION

It is an object of this invention to provide a method and apparatus for monitoring in-vivo pump performance as well as in-vivo catheter performance.

It is a further object of this invention to provide a relatively simple technique of monitoring the performance of an in-vivo pump system to provide quantitative data in the diagnosis of potential pump system problems.

Yet another object of this invention is to define a system which, utilizing externally obtained data, evaluates in-vivo pump system performance.

A still further object of this invention is to define a system which, utilizing externally obtained data, evaluates in-vivo port performance.

In accordance with this invention, to determine whether measured flow rate of an in-vivo pump is acceptable, baseline data is required. That is, it is first necessary to determine the expected pump flow rate for a given in-vivo environment. The temperature and pressure conditions that exist in-vivo generally differ from those which are used during bench test flow characterization of a particular pump. In the case of Freon driven continuous flow pumps the expected in-vivo flow rate is a function of three environmental conditions: (1) Freon pressure; (2) fluid viscosity; (3) the pressure present at the catheter inlet. Having measured the pressure and flow characteristics of the pump under in-vitro conditions, the expected in-vivo flow rate can then be recalculated utilizing the measured values of the in-vivo pump environment. This invention provides the algorithm and system hardware to achieve that goal.

For purposes of diagnostic testing of in-vivo catheter performance, measurements are required that are indicative of both the dynamic and static flow resistances. The static flow resistance can be determined from steady back pressure created by a steady flow through the catheter. The dynamic resistance measurement, however, requires the injection of a pressure disturbance into the catheter inlet. The response to this pressure disturbance is indicative of dynamic resistance in the catheter.

The system preferably comprises components for measuring side port/port pressure and a second pressure transducer to measure pump reservoir pressure. A barometric pressure transducer is employed to obtain baseline environmental data. A pump syringe driver is used to prime a fluid path to deliver a pressure disturbance to the catheter. A processor/controller is used to implement the operating algorithm with operator interface and utilizes digital display and printer technology for prompting messages, data display and obtaining hard copies. Those components operate in accordance with a functional algorithm to be defined herein such that appropriate parameters and calculations are made to determine pump and catheter performance.

This invention will be described in greater detail by reference to the attached drawings and the description that follows.

DESCRIPTION OF THE PREFERRED EMBODIMENT

Figure 1:
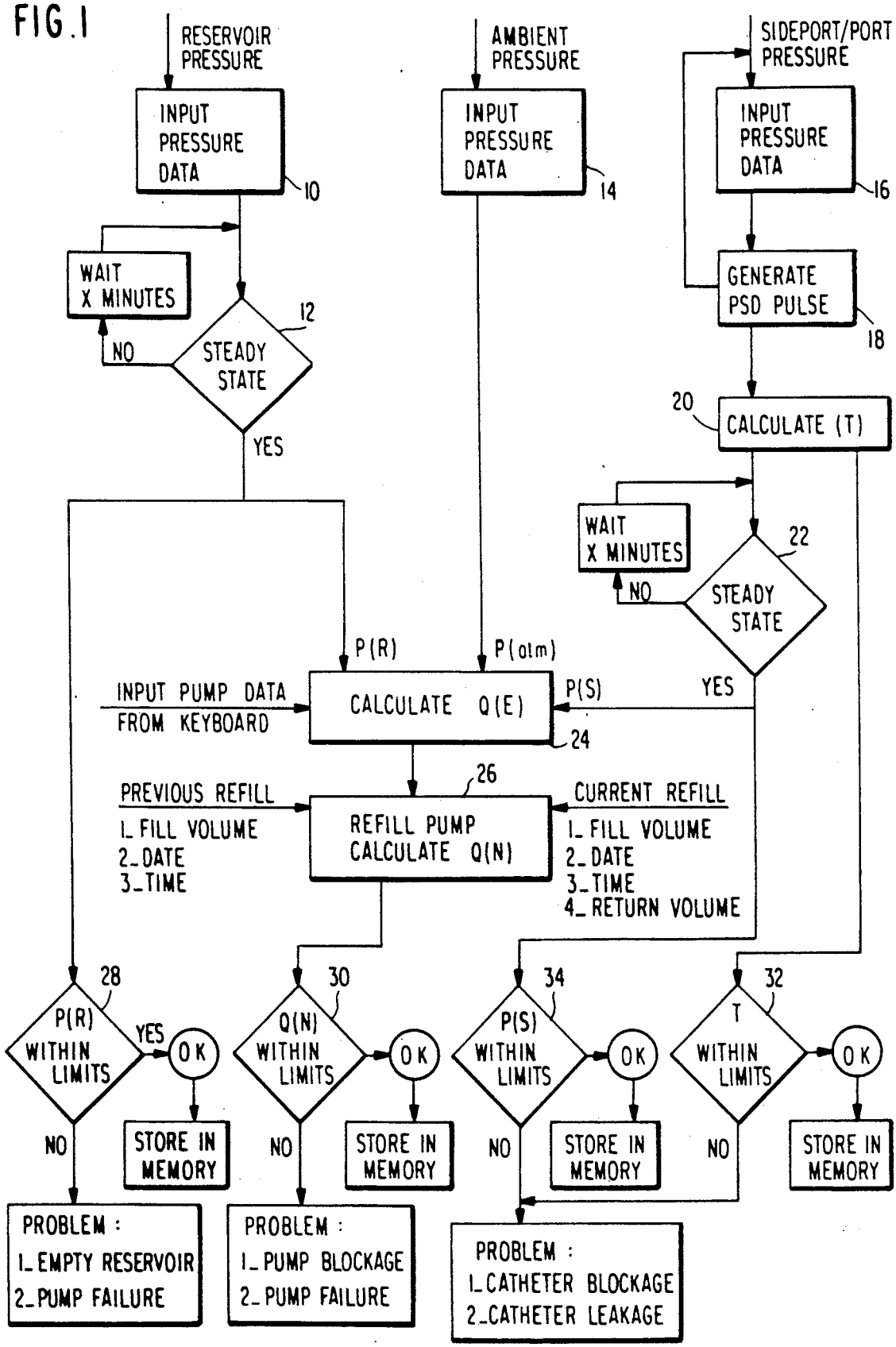
FIG. 1 is a block diagram of the algorithm used to obtain pump/catheter diagnostic data.

Referring now to FIG. 1, a functional algorithm of the system in accordance with this invention is depicted. The procedure would utilize a subject having an implanted infusion device, the subject awake and placed in a room having a temperature environment approximating that which the subject would normally experience. Pump data, that is production data, is a "given" in the procedure. That production data includes the reservoir pressure at 50 ml, psia (P(50)); the reservoir pressure at 4 ml, psia (P(4)) and the water flow rate at 37° C., ml/day (Q(I)). At an appropriate step in the procedure, such pump data would be input. Using a Huber needle, together with disposable plastics, the fluid flow path is primed. All air bubbles are removed from the fluid path prior to calibration of a pressure transducer. Once the skin site over the pump reservoir septum and the pump sideport septum has been prepared, needle penetration takes place into the pump reservoir to record a pressure read out.

Thus, as illustrated in FIG. 1, an initial step is to obtain pressure readings from the implanted pump reservoir. Block 10 basically indicates this step which occurs on an iterative basis until steady state pressure readings are obtained. That is, utilizing a digital readout, strip chart or the like, once initial pressure readings are obtained, a determination is made, that is a decision at block 12 as to whether the pressure readings are in a steady state or not. If not, pressure readings are taken over a period of time (x minutes) until steady state thermodynamic conditions are achieved.

A second initial step is to obtain ambient pressure data at block 14 utilizing a barometric pressure transducer.

A third initial input is a determination of the sideport pressure. Such is used to determine catheter function. A needle then penetrates into the sideport septum and pressure data P(S) indicative of sideport pressure is obtained. Such is illustrated at block 16. Then, the pressure disturbance pulse can be generated by the introduction of pressure disturbance via the sideport into the catheter. Once this pulse has been generated, depicted at block 18, the decay time (T) can be ascertained at block 20. The decay time in seconds is measured after the generation of the disturbance pulse illustrated at block 18.

In accordance with this invention, the expected flow rate from the implanted pump is then determined. This determination is made based on the use of production data from the implanted pump which was taken prior to implantation. Such pump data is input into the system via a keyboard and comprises reservoir pressures at 50 ml and 4 ml together with the measured water flow rate in ml/day at 37° C. The expected flow rate is based on the following five facts and/or assumptions:

(1) the viscosity of water at 37° C. = 0.72 cp in the case of water based medications. For others, an appropriate viscosity will be chosen;
(2) the average atmospheric pressure existing at the time production data was taken approximates 14.6 psia;
(3) the average pump bellows characteristics approximates the characteristics of each bellows comprising the component of an implantable pump;
(4) the reservoir pressure at half reservoir volume approximates the average reservoir pressure during the flow cycle; and
(5) the measured reservoir pressure approximates the average reservoir pressure at half reservoir volume.

Thus, the reservoir pressure P(V) psia as a function of the Centigrade temperature (t) can be calculated based on a reservoir volume of 0.5 full.

$$P(V) = [0.70873 * t - 3.305].$$

Now assume that $P(V) = [P(4) + P(50)] * 0.5$.

Water viscosity as a function of Centigrade temperature (t) can be determined wherein, water viscosity (U) = inverse log $[12.221/t - 0.475]$.

Resolving those equations, the expected flow rate, Q(E) can be determined as:

$$Q(E) = Q(I) * ([P(R) - P(S)]/[P(V) - 14.6]) * (0.72/U)$$

$$Q(E) = Q(I) * [P(R) - P(S)]/[P(V) - 14.6]) * (0.72/\text{inverse log } X)$$

where, $X = (8.661/[P(R) + P(ATM) + 3.305] - 0.475)$
and, where, $P(V) = [P(4) + P(50)] * 0.5$ Once Q(E) is calculated at box 24 then, the normalized flow rate Q(N) can be calculated. The normalized flow rate is derived from the current pump refill/flow rate measurement and the expected pump flow rate calculation. This calculation is made in box 26 based on previous volume data, intervals between refills and current refill data.

Based on the calculations of Q(N) together with the values of P(R), P(S) and the decay time T, various decisions can be made concerning the functioning of the system. The expected limits for the above parameters are a function of the individual device calibrated performance and the environment of use. The calibrated performance is in turn the historical data maintained for each individual unit and available to the diagnostician. Expected limits are a function of individual device calibrated performance and the environment of use. If the reservoir pressure P(R) is within expected limits, then the data can be stored in a memory based on a conclusion that the pump reservoir is operating satisfactorily. This decision at block 28 carries with it a converse conclusion. That is, if P(R) is not within normal limits then, the problem may be either an empty reservoir, insufficient medication or, pump failure. The problem can be resolved by measuring the return volume, attempting to fill the reservoir, and determining whether or not the value of P(R) is restored to within normal limits.

If the normalized flow rate Q(N) is within expected limits as determined at block 30, then that calculated value is stored in memory and operation is presumed to be normal. If, however, the value of Q(N) is not within expected limits, then either a pump blockage has occurred, or a pump failure has been indicated. In either case, the diagnosis for such a problem would require explant of the pump.

If the decay time T is within expected limits then the decision at block 32 would simply store the decay time 32 in memory for future use. If the sideport pressure P(S) is within expected limits, then the decision block at element 44 would simply then have the value of P(S) stored in memory for future use. If both decay time T and sideport pressure P(S) are within expected values, then proper catheter operation is assured. If, however, either value of the decay time T or pump sideport pressure P(S) is not within expected limits, either catheter blockage or catheter leakage can be presumed. Injection of a contrast agent through the sideport can detect catheter leakage problems. Catheter blockages may sometimes be removed by flushing through the sideport. Retest if this remedy fails, then recatheterization is required.

It can, therefore, be seen that by utilizing the methodology of FIG. 1 a differentiation between pump problems and catheter problems can be obtained based on making simple input measurements from the pump and sideport septums. To achieve such measurements, a device illustrated functionally in FIG. 2 may be employed. Schematically illustrated are a pair of septums 50 and 51. The sideport or separate port septum 50 and the pump reservoir septum 51 are a part of the implanted pump system. They are, however, accessed via a pair of needles 52, 54. Those needles penetrate the skin and provide a sterile fluid passageway for making various measurements. Needle 52 is in fluid communication with a pressure transducer 56 used to measure a side port/port pressure. A pump syringe driver 58 is used for priming the fluid path and delivering the pressure disturbance pulse to the catheter.

Needle 54 provides a fluid passage to a transducer 60 used to measure pump reservoir pressure. By means of a two-way stopcock 62, a refill syringe 64 may be placed on line for purposes of introducing a refilling dose of medication into the pump reservoir.

Figure 2:
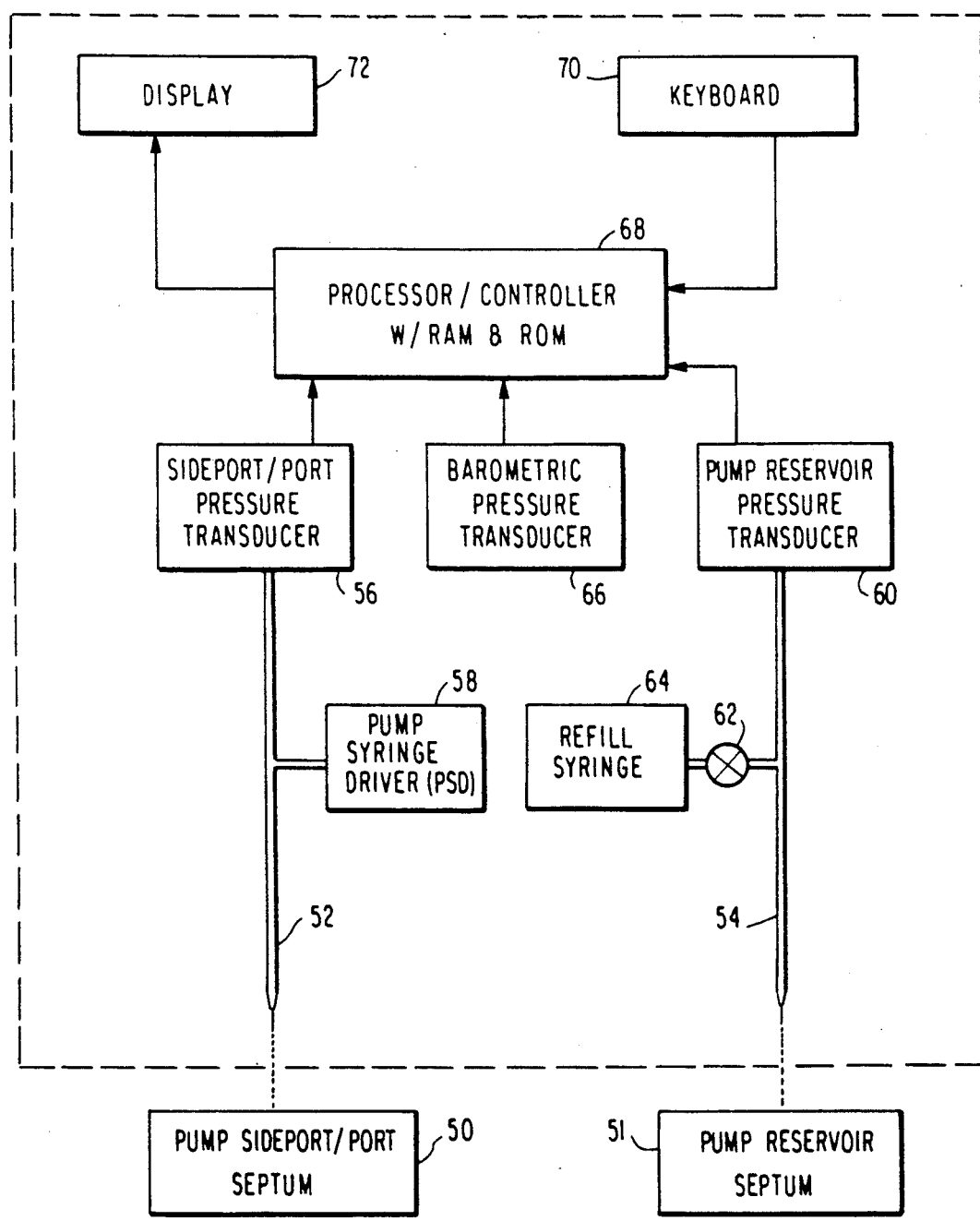
FIG. 2 is a functional block diagram of the components used to perform the algorithm of FIG. 1.

The third transducer 66 is used to obtain barometric pressure readings. As illustrated in FIG. 2, the outputs of the transducers 56, 60, and 66 are delivered as input signals into a processor/controller 68. This electronic device is a conventionally provided processor having both RAM and ROM capabilities for various memory functions. The processor 68 performs the calculations of the delay time T, the flow rate calculations Q(E) and Q(N). As can be appreciated, those calculations are preprogrammed functions stored in the ROM section based on the equations as set forth herein. As further input to the processor 68, a keyboard 70 is used to provide input pump data. The RAM section of the controller 68 retains those measured values of P(R), Q(N), P(S), and T when such values are within expected limits. The values are thus stored in the RAM for archival use and for comparison based on averaging techniques when new procedures are carried out. Thus, by recalling those values, the decisions at blocks 28, 30, 32, and 34 are made based on real time measurements when compared with those stored values.

The procedure for analyzing a port is a subset of the above pump system procedure. Only port access is required and calculation of the T and P(S) parameters as illustrated in block 20 and as an input to block 24, are needed. Once T and P(S) are determined, an analysis of catheter performance as made in blocks 23 and 34 can be obtained. Thus, in accordance with this invention, a separate analysis of port performance can be made.

For purposes of output, a display 72 is employed. The display may be a printer, an LED, LCD or other well known display associated with conventional processor technology.

It is apparent that modifications in details of this invention may be made without departing from the essential scope thereof.

Having described my invention, I claim:

1. A system for evaluating operation of an in-vivo medication delivery device having a medication reservoir with a fluid therein for delivery, a separate access port and an outlet in fluid communication thereto comprising:
    means for detaining ambient pressure,
    means for determining an in-vivo pressure in said reservoir,
    means for determining a pressure in said medication delivery device at a posit in a flow path of said fluid downstream of said reservoir, and
    means receiving values representative of said in-vivo pressure, said pressure downstream of said reservoir and ambient pressure to determine whether said medication delivery device is functioning within predetermined limits.

2. The system of claim 1 wherein said means to determine whether said medication delivery device is functioning within predetermined limits comprises means to determine whether said reservoir requires refilling.

3. The system of claim 1 wherein said means to determine whether said medication delivery device is functioning within predetermined limits comprises means to determine whether said outlet is blocked or leaking.

4. The system of claim 1 wherein said means to determine whether said medication delivery device is functioning within predetermined limits comprises means to determine whether said reservoir is releasing medication to said outlet at a predetermined rate.

5. The system of claim 1 wherein said means to determine the pressure in said reservoir comprises a needle and a pressure transducer, said needle penetrating into said reservoir and said pressure transducer producing an output signal that is input to said means to determine whether said medication delivery device is functioning within predetermined limits.

6. The system of claim 1 further comprising means for inputting data as to previous performance and refill data for the medication delivery device under evaluation into said means to determine whether said device is functioning within predetermined limits.

7. The system of claim 6 wherein said means to determine whether said device is functioning within predetermined limits comprises processor means, said processor means including a read only memory storing equations used to determine device performance and a random access memory for storing determined pressure values and input data.

8. A method of evaluating operation of an in-vivo medication delivery device having a medication reservoir having a fluid for delivery in-vivo, an access port and an outlet in fluid communication thereto, comprising the steps of:
    determining, ambient pressure, in-vivo reservoir pressure and in-vivo pressure in said delivery device at a point downstream of said reservoir, and
    evaluating, based on the determined pressures, whether said in-vivo device is functioning within predetermined limits.

9. The method as in claim 8, wherein said step of evaluating comprises the step of determining whether said medication reservoir is depleted or has failed to deliver medication.

10. The method as in claim 8, wherein said step of evaluating comprises the step of determining whether said outlet is leaking or is blocked.

11. The method as in claim 8 wherein said step of evaluating comprises the step of determining an expected flow rate of said medication delivery device as a function of determined pressures and calibration data for a particular device under evaluation.

12. The method as in claim 11, further comprising the step of determining a normalized flow rate for said device based on the determination of the expected flow rate and data relating to refill volumes and intervals between refills.

13. The method as in claim 8, wherein the determination of in-vivo pressure at a point in a flow path of said fluid downstream of said reservoir comprises the steps of puncturing said access port with a needle, generating a pressure disturbance pulse in said outlet and measuring a decay time of said pressure disturbance pulse.

14. The method as in claim 8 further comprising the steps of calculating a normalized flow rate for said device and storing said flow rate.

15. A method of determining whether an implanted medication delivery device is functioning within predetermined limits comprising the steps of measuring ambient pressure:

determining a normalized flow rate for said device based on in-vivo pressure measurements, calibration data and device refill data, and determining, without explant of said device, whether said device requires refill or has malfunctioned.

16. The method as in claim 15 further comprising the step of generating a pressure disturbance pulse in an outlet of said device, measuring a decay time of said pulse, and determining whether said outlet is blocked or is leaking.

17. The method as in claim 15 further comprising the step of measuring in-vivo pressure of a reservoir of said device and in-vivo pressure at a point in said device in a flow path for said fluid between said reservoir and an outlet.

18. A method of determining whether an implanted medication delivery device is functioning within normal limits comprising the steps of measuring ambient pressure:

measuring a flow resistance based on in-vivo measurements, and determining, without explant of said device, whether said device is dispensing medication within predetermined limits.

19. The method as in claim 18 wherein said step of measuring flow resistance comprises steps of measuring a steady state in-vivo pressure in said device and generating a pressure disturbance pulse in said device and measuring a decay time thereof.

20. The method as in claim 18 wherein the step of determining whether said device is dispensing medication within predetermined limits comprises determining whether said device is blocked or is leaking.

21. A system for evaluating operating of an in-vivo medication delivery device having an access port and an outlet comprising:

means in fluid communication with said device for determining a steady state in-vivo pressure in said device, means in fluid communication with said device for generating a pressure disturbance pulse in said device and determining a decay time thereof, and means responsive to said means for determining a steady state in-vivo pressure and said means for generating a pressure disturbance for determining whether said device is functioning within predetermined limits.

22. The system of claim 21 wherein said means to determine whether said device is functioning within predetermined limits comprises means receiving values of said steady state pressure and said decay time and determining whether said device is blocked or is leaking.

* * * * *